(12) United States Patent
Olsen

(10) Patent No.: US 7,981,107 B2
(45) Date of Patent: Jul. 19, 2011

(54) LOW PROFILE INLET VALVE FOR A PISTON PUMP THERAPEUTIC SUBSTANCE DELIVERY DEVICE

(75) Inventor: James M. Olsen, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1285 days.

(21) Appl. No.: 11/435,582

(22) Filed: May 17, 2006

(65) Prior Publication Data

US 2006/0206099 A1      Sep. 14, 2006

Related U.S. Application Data

(62) Division of application No. 09/953,527, filed on Sep. 14, 2001, now Pat. No. 7,066,915.

(60) Provisional application No. 60/282,778, filed on Apr. 10, 2001.

(51) Int. Cl.
*A61M 1/00* (2006.01)
*A61M 31/00* (2006.01)
*A61M 37/00* (2006.01)
*A61K 9/22* (2006.01)

(52) U.S. Cl. .......... 604/891.1; 604/288.04; 604/152

(58) Field of Classification Search .......... 604/151, 604/152, 154, 95.02, 95.01, 65–67, 288.01–288.04, 604/93.01, 890.1, 891.1, 892.1; 128/DIG. 12, 128/DIG. 13; 417/416, 417, 549, 550
See application file for complete search history.

(56) References Cited

U.S. PATENT DOCUMENTS

| | | | |
|---|---|---|---|
| 3,846,682 A | 11/1974 | Massie | |
| 4,071,042 A | 1/1978 | Lombard et al. | |
| 4,102,610 A | 7/1978 | Taboada et al. | |
| 4,210,409 A | 7/1980 | Child | |
| 4,541,787 A | 9/1985 | DeLong | |
| 4,568,250 A | 2/1986 | Falk et al. | |
| 4,569,641 A | 2/1986 | Falk et al. | |
| 4,573,994 A | 3/1986 | Fischell et al. | |
| 4,604,090 A * | 8/1986 | Reinicke | 604/118 |
| 4,636,150 A | 1/1987 | Falk et al. | |

(Continued)

FOREIGN PATENT DOCUMENTS

EP      0605903 A1      7/1994

(Continued)

OTHER PUBLICATIONS

Brochure, "SynchroMed® Infusion System: Optimizing Therapy Through Programmability," Medtronic, Inc., 1995.

(Continued)

*Primary Examiner* — Matthew F Desanto
(74) *Attorney, Agent, or Firm* — Mueting, Raasch & Gebhardt, P.A.

(57) ABSTRACT

Low profile inlet valve embodiments for a piston pump therapeutic substance infusion device are disclosed that reduce dead volume, occupies little residential space, operates rapidly, and have many other improvements. The therapeutic substance infusion device has a housing, a therapeutic substance reservoir, a power source carried in the housing, electronics, a piston pump, and an inlet valve. The piston pump is configured for pumping therapeutic substance from the therapeutic substance reservoir through an infusion port at a programmed rate. The inlet valve is in fluid communication with a reservoir outlet to control the flow of therapeutic substance into the piston pump. The inlet valve has a substantially coplanar valve surface and valve spring. Many embodiments of the low profile inlet valve and its methods of operation are possible.

27 Claims, 16 Drawing Sheets

U.S. PATENT DOCUMENTS

| | | |
|---|---|---|
| 4,690,371 A | 9/1987 | Bosley et al. |
| 4,714,462 A | 12/1987 | DiDomenico |
| 4,775,301 A | 10/1988 | Cartwright et al. |
| 4,883,467 A | 11/1989 | Franetzki et al. |
| 4,965,864 A | 10/1990 | Roth et al. |
| 4,985,015 A | 1/1991 | Obermann et al. |
| 5,085,563 A | 2/1992 | Collins et al. |
| 5,318,521 A | 6/1994 | Slettenmark |
| 5,434,549 A | 7/1995 | Hirabayashi et al. |
| 5,472,323 A * | 12/1995 | Hirabayashi et al. ......... 417/417 |
| 5,509,792 A * | 4/1996 | Sullivan et al. ............... 417/417 |
| 5,707,361 A | 1/1998 | Slettenmark |
| 5,758,666 A | 6/1998 | Larson, Jr. et al. |
| 5,797,733 A | 8/1998 | Falk et al. |
| 5,833,440 A | 11/1998 | Berling |
| 5,915,929 A | 6/1999 | Falk et al. |
| 5,921,526 A | 7/1999 | Najmolhoda |
| 5,947,155 A | 9/1999 | Miki et al. |
| 6,770,067 B2 | 8/2004 | Lorenzen et al. |
| 7,066,915 B2 | 6/2006 | Olsen |
| 2002/0173772 A1 | 11/2002 | Olsen |
| 2002/0173773 A1 | 11/2002 | Olsen |
| 2004/0022654 A1 | 2/2004 | Ishida |
| 2004/0220553 A1 | 11/2004 | Olsen |

FOREIGN PATENT DOCUMENTS

| | | |
|---|---|---|
| EP | 0791369 A1 | 8/1997 |
| JP | 55142981 | 7/1980 |

OTHER PUBLICATIONS

"Valves, Piping & Pipelines Handbook," Elsevier Advanced Technology XP002200965, ISBN: 1 85617 252 X, Chapter Entitled Cavitation, pp. 658-666.

* cited by examiner

LOW PROFILE INLET VALVE FOR A PISTON PUMP THERAPEUTIC SUBSTANCE DELIVERY DEVICE

RELATED APPLICATION

This is a divisional of application Ser. No. 09/953,527, filed Sep. 14, 2001, (pending), which is incorporated herein by reference and which claims the benefit of provisional application U.S. Ser. No. 60/282,778, filed Apr. 10, 2001, entitled "LOW PROFILE INLET VALVE FOR A PISTON PUMP THERAPEUTIC SUBSTANCE DELIVERY DEVICE" by James M. Olsen.

This disclosure is related to the following co-pending applications entitled "PERMANENT MAGNET SOLENOID PUMP FOR AN IMPLANTABLE THERAPEUTIC SUBSTANCE DELIVERY DEVICE" by inventor Olsen (Application No. 60/282,775; filed Apr. 10, 2001) and "IMPLANTABLE THERAPEUTIC SUBSTANCE DELIVERY DEVICE HAVING A PISTON PUMP WITH AN ANTI-CAVITATION VALVE" by inventor Olsen (Application No. 60/282,777; filed Apr. 10, 2001) which are not admitted as prior art with respect to the present disclosure by its mention in this section.

BACKGROUND OF THE INVENTION

This disclosure relates to a medical device and more particularly to an implantable therapeutic substance delivery device, also known as an implantable drug pump, with a piston operated pump.

The medical device industry produces a wide variety of electronic and mechanical devices for treating patient medical conditions such as pacemakers, defribulators, neurostimulators, and therapeutic substance delivery pumps. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a filler life. Implantable drug delivery pumps can be used to treat conditions such as pain, spasticity, cancer, and a wide variety of other medical conditions.

An implantable drug delivery pump is implanted by a clinician into a patient at a location appropriate for the therapy that interferes as little as practicable with patient activity such as subcutaneous in the lower abdomen. Typically, a drug delivery catheter is connected to the drug pump outlet and implanted to infuse the drug, infusate or other therapeutic substance at a programmed infusion rate and predetermined location to treat the medical condition. Reliable and accurate operation of the drug pump is important because both inadequate and unintended therapeutic substance delivery can create patient complications. Many drug pumps are configured, so the pump can be replenished with drug through a refill port or septum while the pump is implanted, so the period the pump can be implanted may not be limited by drug capacity. In electrically powered implantable drug pumps, the period the pump can be implanted is often limited by factors such as battery consumption, corrosive damage, and mechanical wear. The relative large size of some implantable drug pumps can limit locations where the device can be implanted in a patient. An example of an implantable drug pump is shown in Medtronic, Inc. "SynchroMed® Infusion System" Product Brochure (1995). Implantable drug pumps can use a variety of pumping mechanism such as a piston pump, rotary vane pump, osmotic pump, Micro Electro Mechanical Systems (MEMS) pump, diaphragm pump, peristaltic pump, and solenoid piston pump to infuse a drug into a patient.

Solenoid pumps such as variable reluctance solenoid pumps and permanent magnet solenoid pumps operate by applying an electromagnetic force to a pump piston. The electromagnetic force imparts movement to the pump piston to pump fluid from a pumping chamber into an outlet. The fluid flowing into a pumping chamber is controlled. The fluid flowing into the pumping chamber can be controlled with a flow restrictor or an inlet valve. The flow restrictor typically does not have any moving parts and controls the flow of fluid by impeding fluid flow to a predetermined flow rate. An inlet flow restrictor can cause unintended flow to occur under some circumstances. An example of a previous solenoid pump with an inlet flow restrictor is shown in U.S. Pat. No. 4,883,467 "Reciprocating Pump For An Implantable Medication Dosing Device" by Franetzki et al. (Nov. 28, 1989). The inlet valve typically has moving parts and controls the flow of fluid by opening to permit the flow of fluid and closing to prevent the flow of fluid at a predetermined pressure. Inlet valves geometries typically create dead volumes that can make passing air difficult for the pump. Passively operated inlet valves can unintentionally open under some circumstances creating safety concerns. An example of a previous solenoid pump inlet valve is shown in U.S. Pat. No. 4,636,150 "Low Power Electromagnetic Pump" by Falk et al. (Jan. 13, 1987).

For the foregoing reasons, there is a need for a low profile inlet valve for a piston pump therapeutic substance delivery device that reduces dead volume, occupies little residential space, operates rapidly, and has many other improvements.

SUMMARY OF THE INVENTION

A low profile inlet valve for a piston pump therapeutic substance delivery device reduces dead volume, occupies little residential space, operates rapidly, and has many other improvements. The low profile inlet valve controls the flow of therapeutic substance from a therapeutic substance reservoir into a piston pump with a substantially coplanar valve surface and valve spring. The piston pump is configured for pumping therapeutic substance from the therapeutic substance reservoir through an infusion port at a programmed rate. Electronics are coupled to the piston pump and a power source. A therapeutic substance reservoir supplies the piston pump with therapeutic substance through a reservoir outlet. Many embodiments of the low profile inlet valve for a piston pump therapeutic substance delivery device and its methods of operation are possible.

DETAILED DESCRIPTION OF THE PREFERRED EMBODIMENTS

Figure 1:
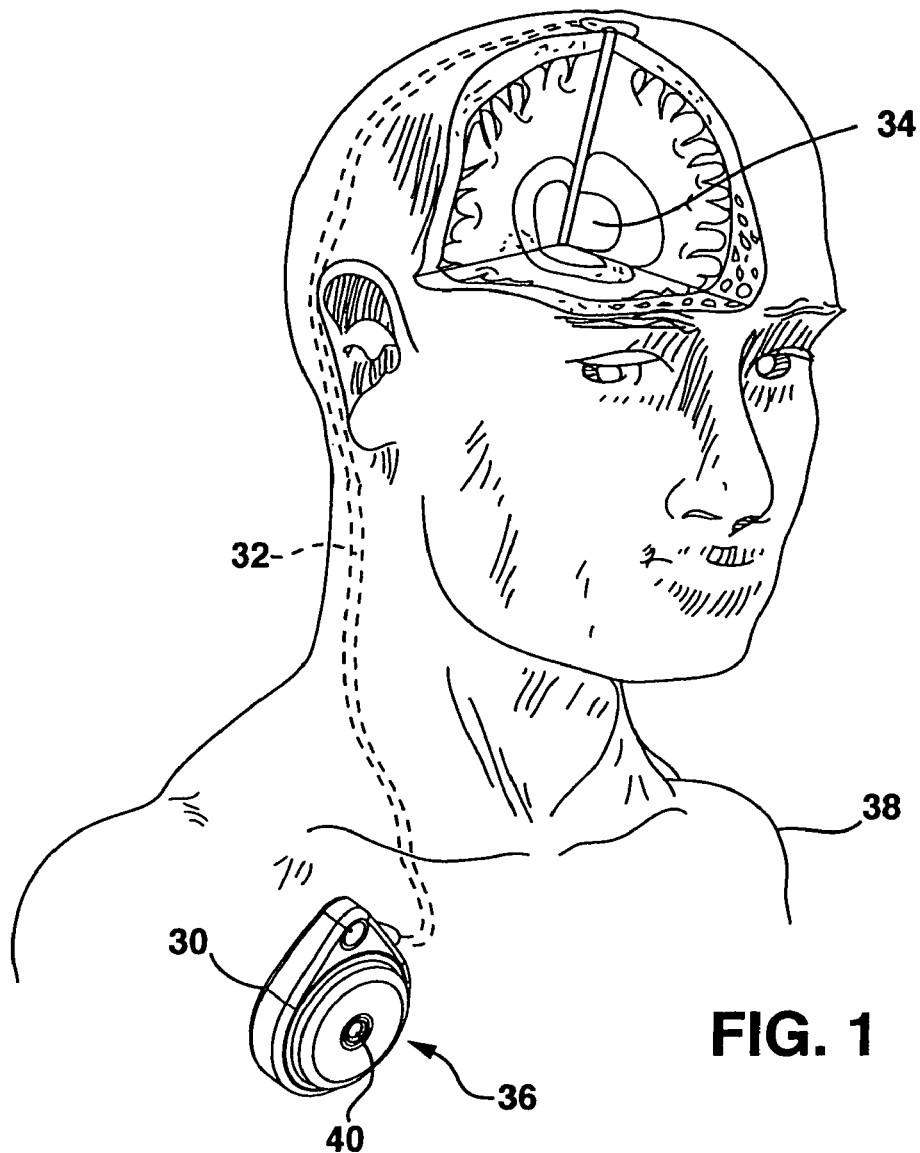
FIG. 1 shows the environment of an implantable therapeutic substance delivery device embodiment.
Figure 2:
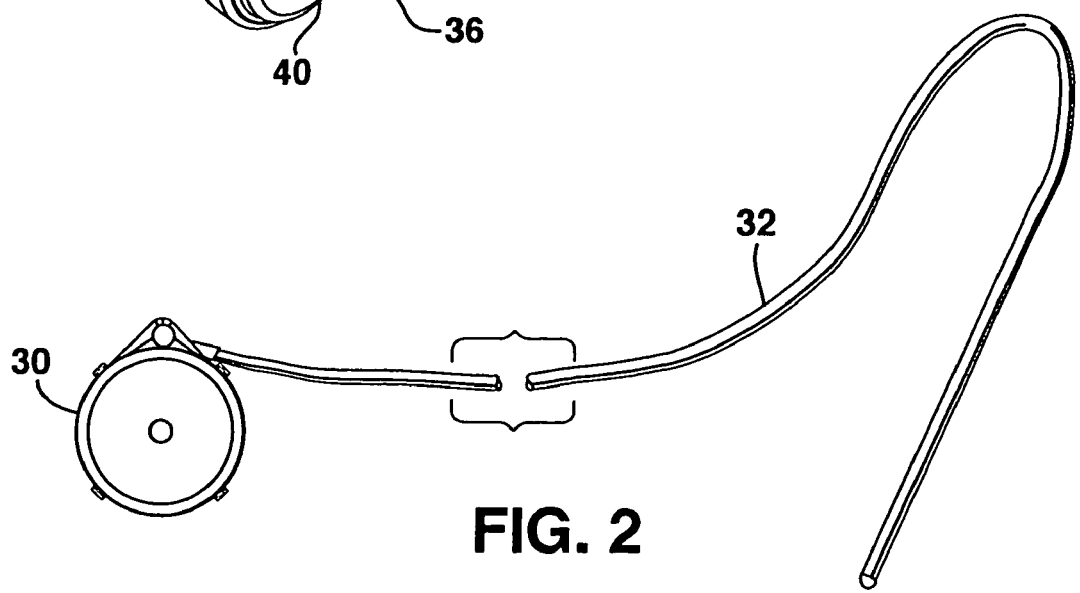
FIG. 2 shows an implantable therapeutic substance delivery device with catheter embodiment.

FIG. 1 shows the environment of an implantable medical device known as an implantable therapeutic substance delivery device 30, also known as a drug pump, having a permanent magnet solenoid pump embodiment. The therapeutic substance delivery device 30 can be used for a wide variety of therapies such as pain, spasticity, cancer, and many other medical conditions. The implantable therapeutic substance delivery device 30 is typically implanted by a clinician such as a surgeon in a sterile surgical procedure performed under local, regional, or general anesthesia. Before implanting the therapeutic substance delivery device 30, a catheter 32 is typically implanted with the distal end position at the desired therapeutic substance delivery site 34 and the proximal end tunneled to the location where the therapeutic substance delivery device 30 is to be implanted. The catheter 32 and the therapeutic substance delivery site 34 can generate a back pressure during infusion known as the infusion site pressure that the therapeutic substance delivery device 30 overcomes to deliver therapeutic substance 36 at the infusion site. The implantable therapeutic substance delivery device 30 is generally implanted subcutaneously about 2.5 cm (1.0 inch) beneath the skin where there is sufficient subcutaneous tissue to support the implanted system. Once the therapeutic substance delivery device 30 is subcutaneously implanted into the patent, the incision can be sutured closed and the therapeutic substance delivery device 30 can begin operation.

The therapeutic substance delivery device 30 operates to infuse a therapeutic substance 36 at a programmed rate into a patient 38. The therapeutic substance 36 is a product or substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like.

The therapeutic substance 36 can be replenished in some embodiments of the implanted therapeutic substance delivery device 30 by inserting a non-coring needle connected to a syringe filled with therapeutic substance 36 through the patient's skin into a septum 40 on the therapeutic substance delivery device 30 to fill the implanted device. If the therapeutic substance delivery device 30 requires replacement due to conditions such as battery depletion or other condition, an incision is made near the implanted therapeutic substance delivery device 30, and the old therapeutic substance delivery device 30 is removed, also known as explanted. After the old therapeutic substance delivery device 30 has been explanted, typically a new therapeutic substance delivery device 30 is then implanted.

Figure 3:
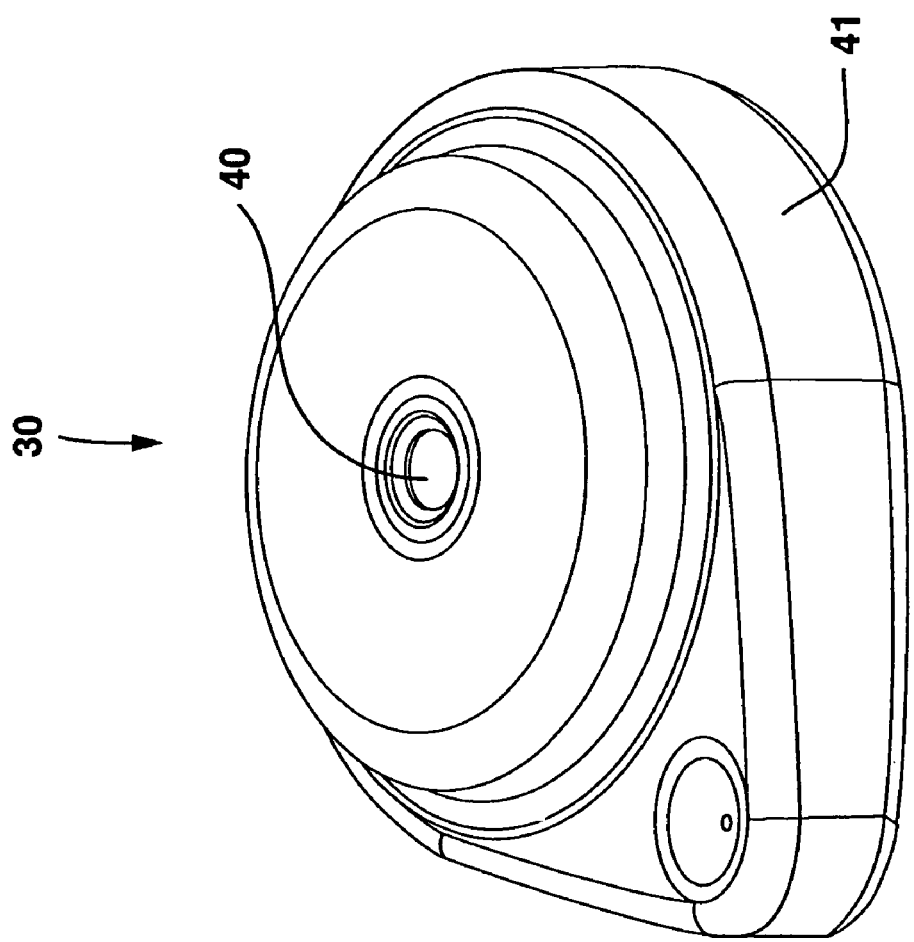
FIG. 3 shows an implantable therapeutic substance delivery device embodiment.
Figure 4:
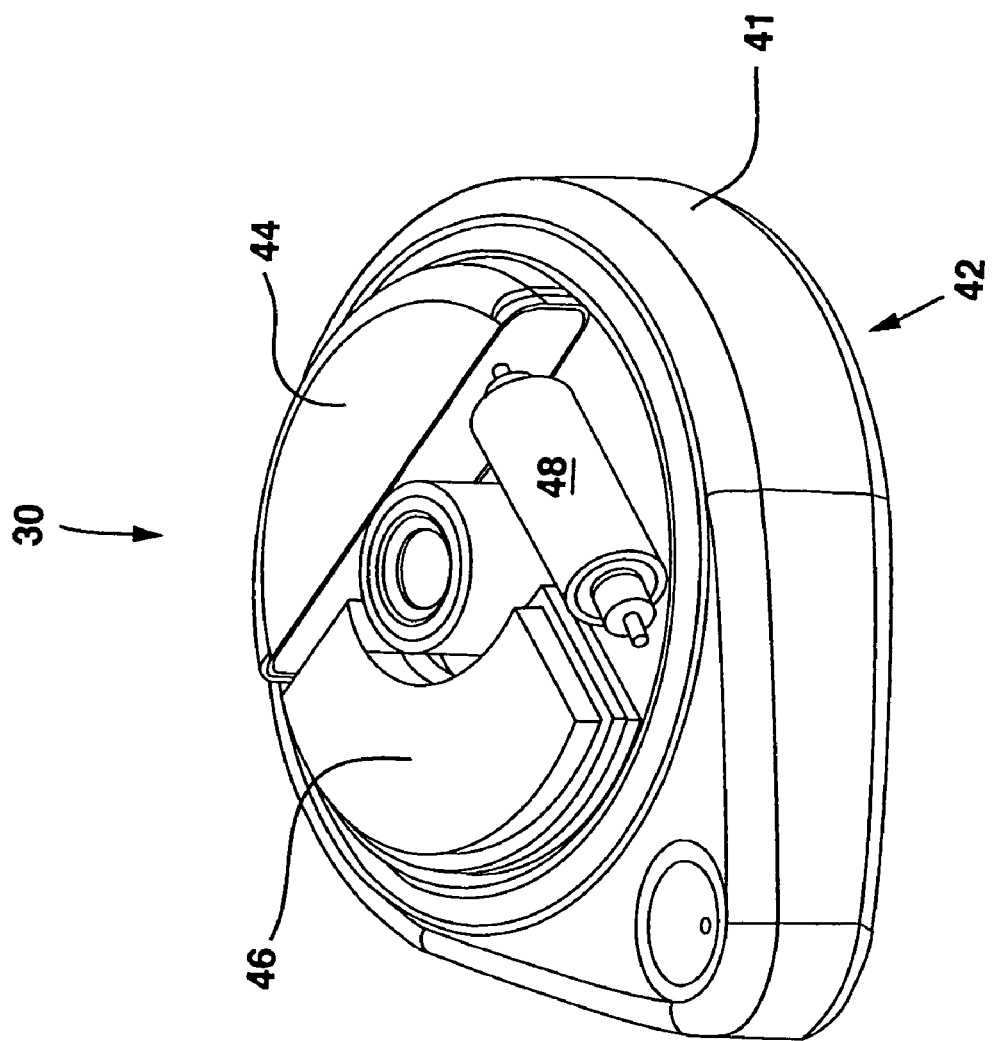
FIG. 4 shows the implantable therapeutic substance delivery device of FIG. 3 with a portion of a housing removed.
Figure 5:
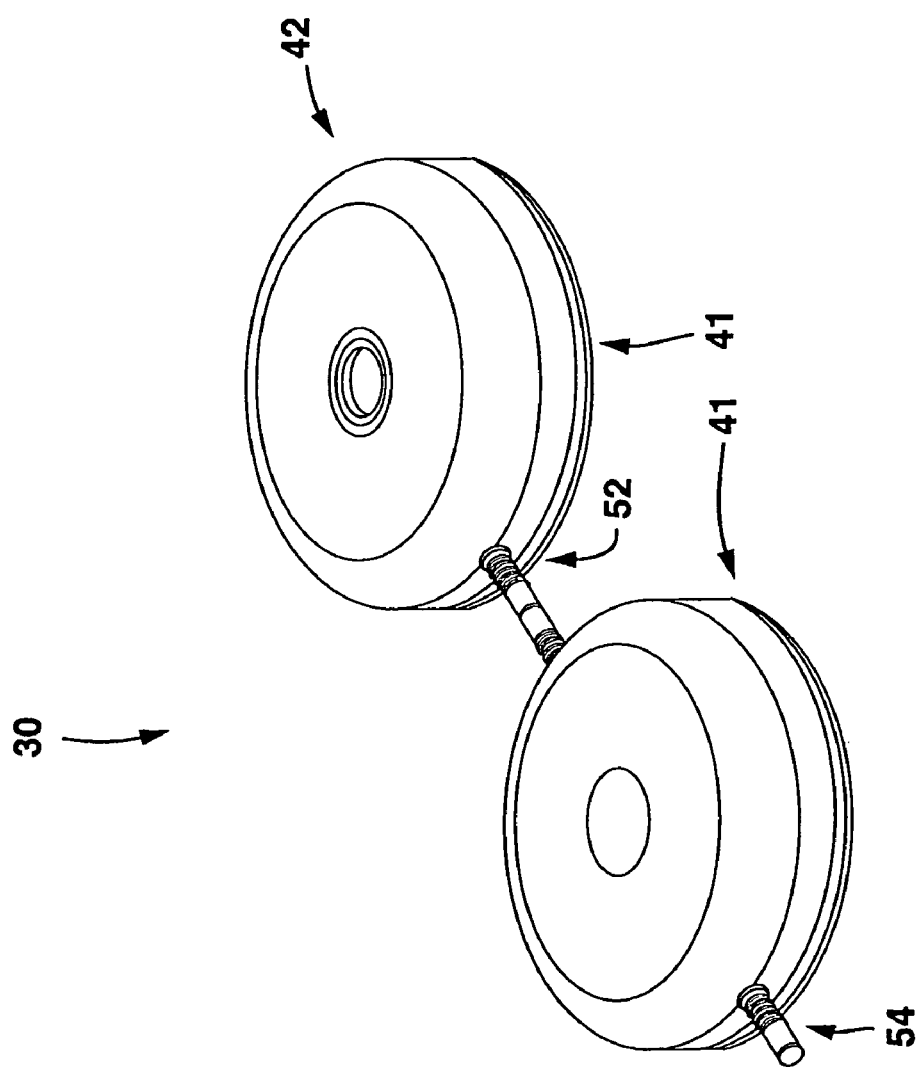
FIG. 5 shows another implantable therapeutic substance delivery device embodiment having a separate therapeutic substance reservoir.
Figure 6:
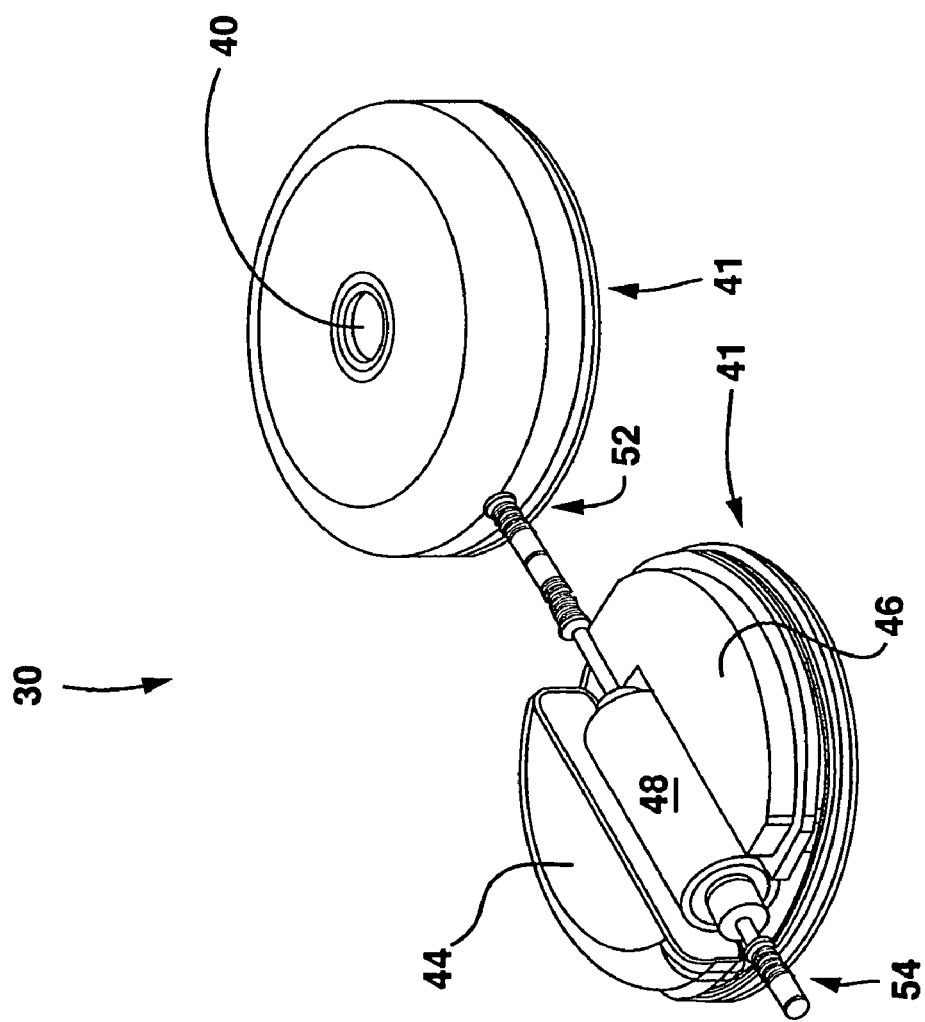
FIG. 6 shows the implantable therapeutic substance delivery device of FIG. 5 with a portion of a housing removed.
Figure 7:
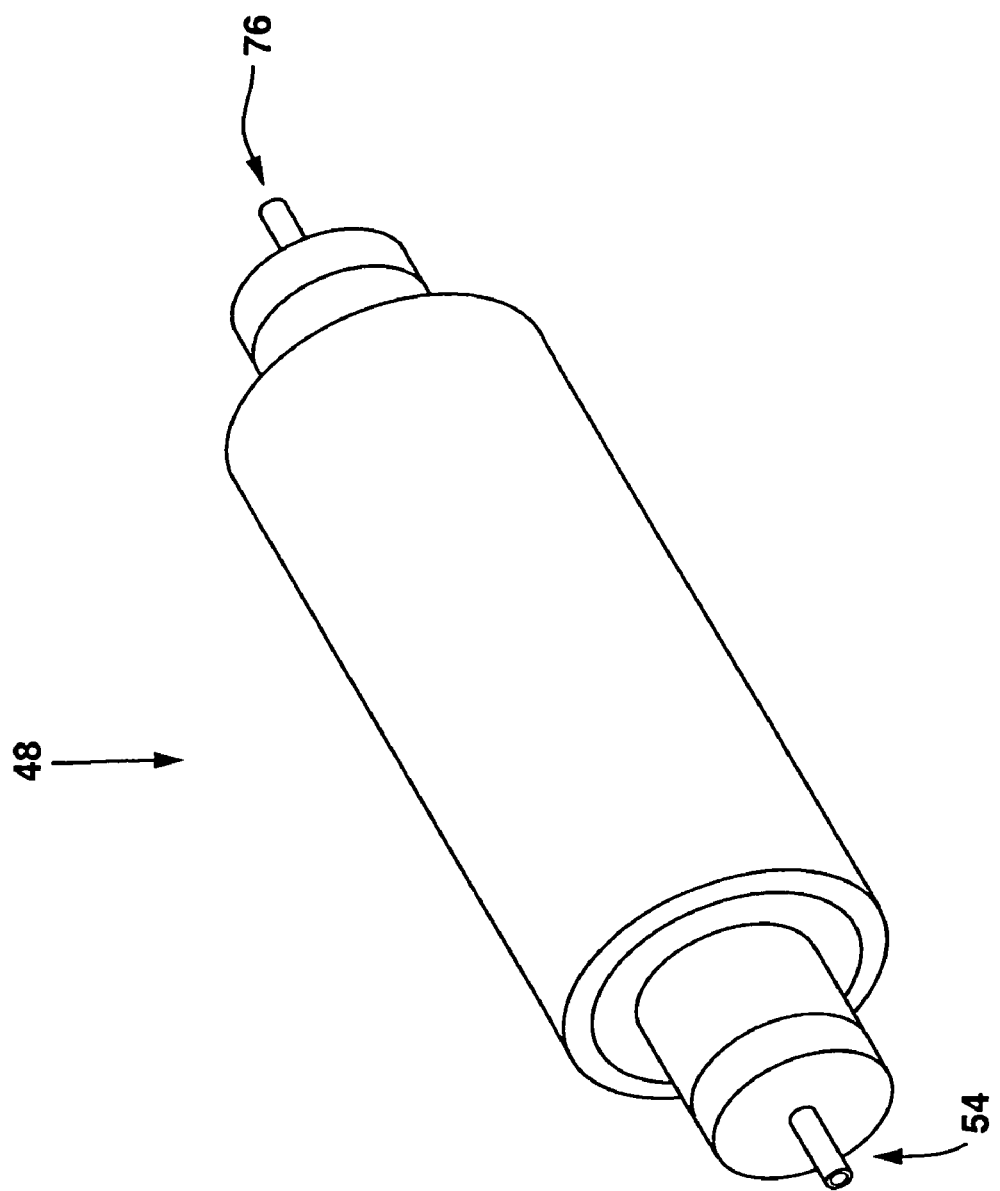
FIG. 7 shows a permanent magnet solenoid pump embodiment.
Figure 8:
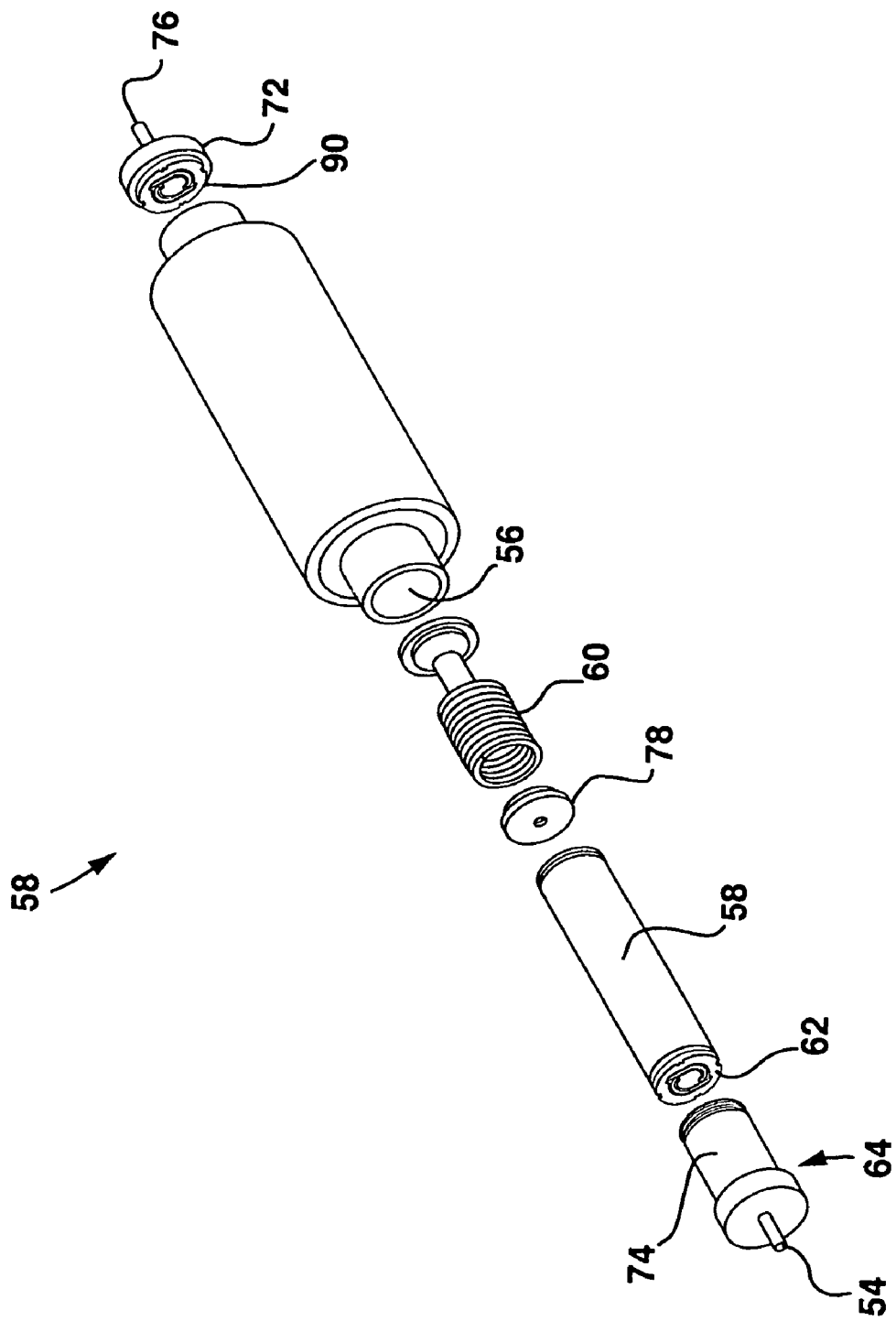
FIG. 8 shows an exploded view of the permanent magnet solenoid pump of FIG. 7 embodiment.
Figure 9:
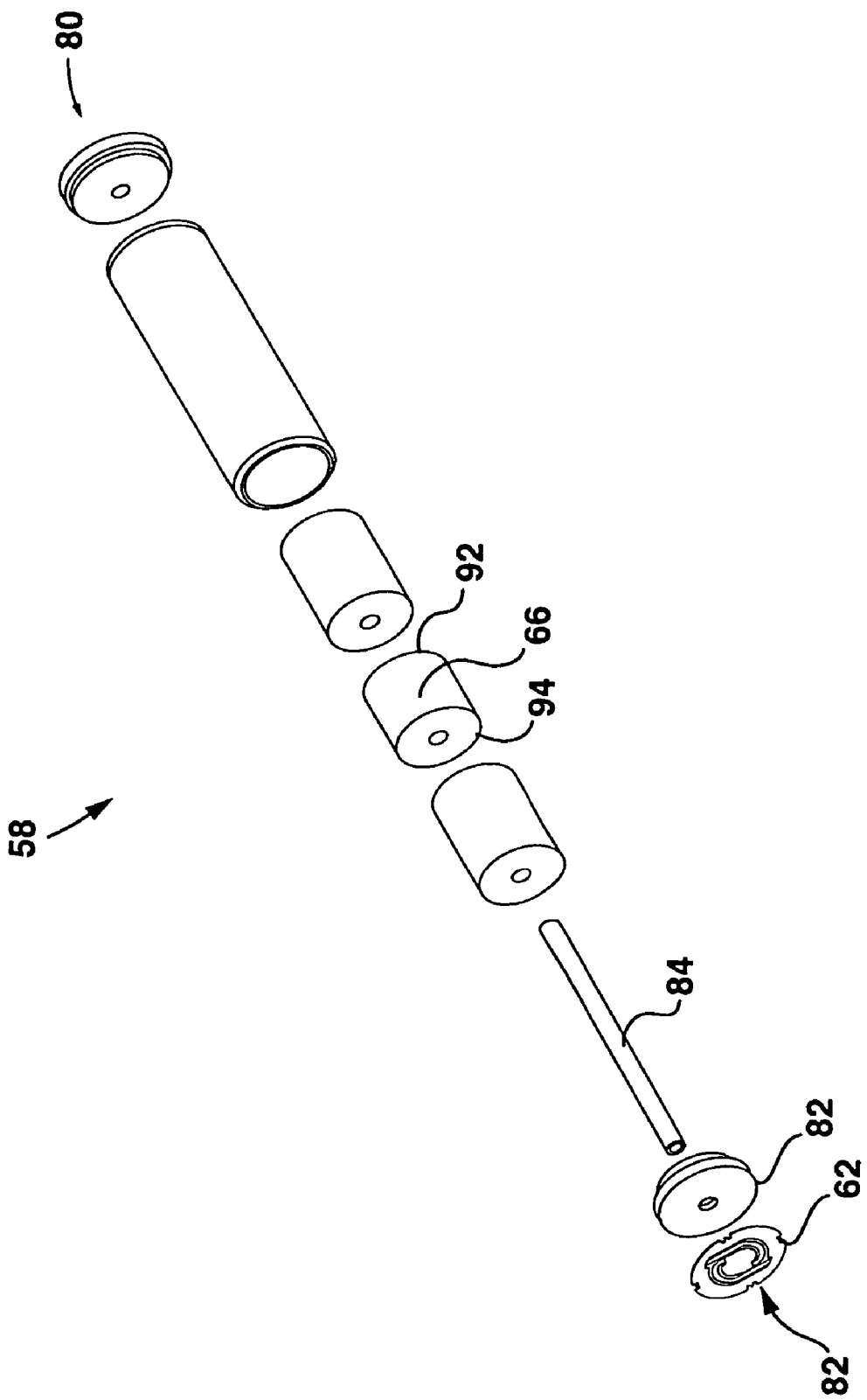
FIG. 9 shows an exploded view of a pump piston for a permanent magnet solenoid pump three-coil embodiment.
Figure 10:
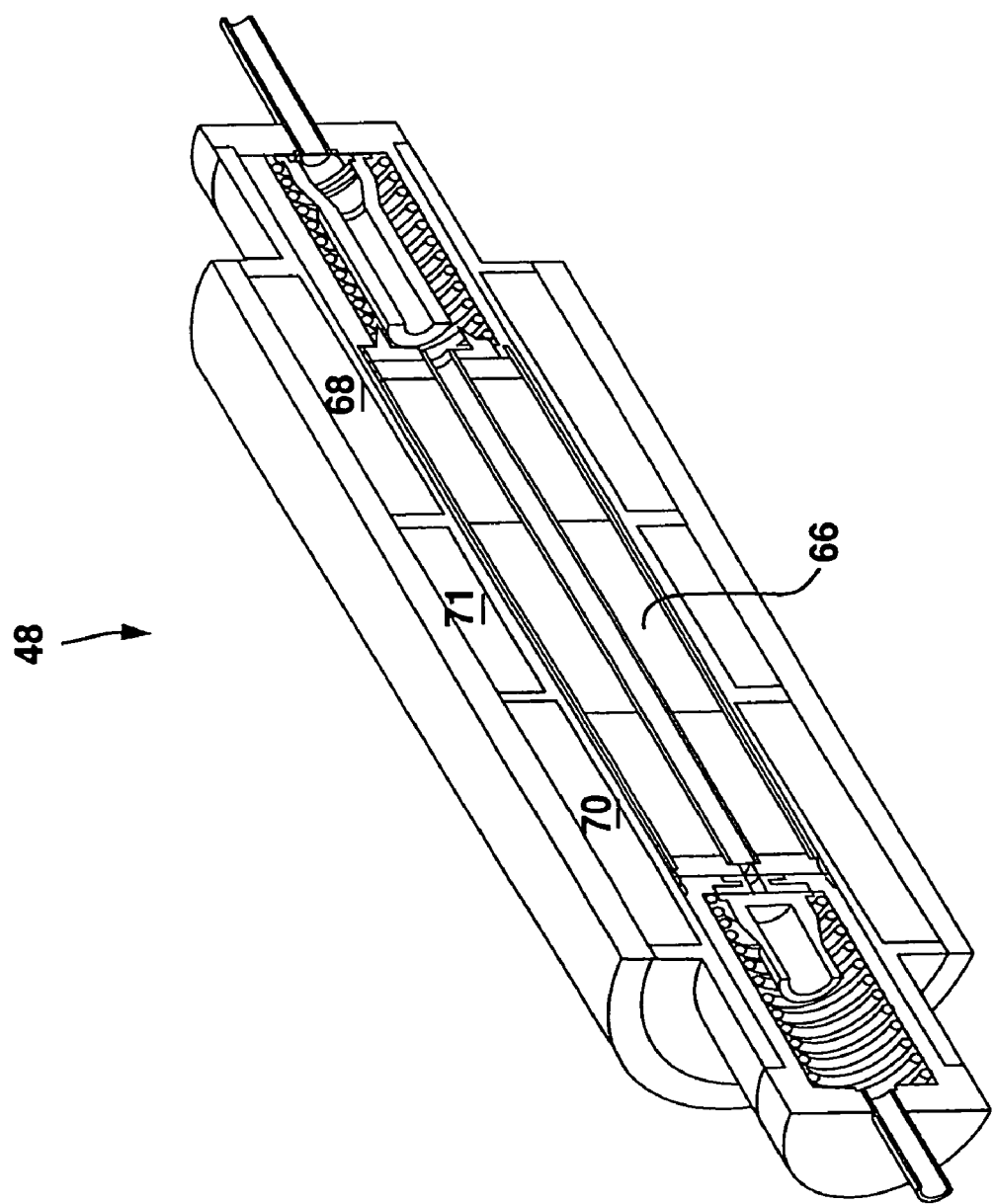
FIG. 10 shows an isometric cross-section view of a pump piston for a permanent magnet solenoid pump three-coil embodiment.
Figure 11:
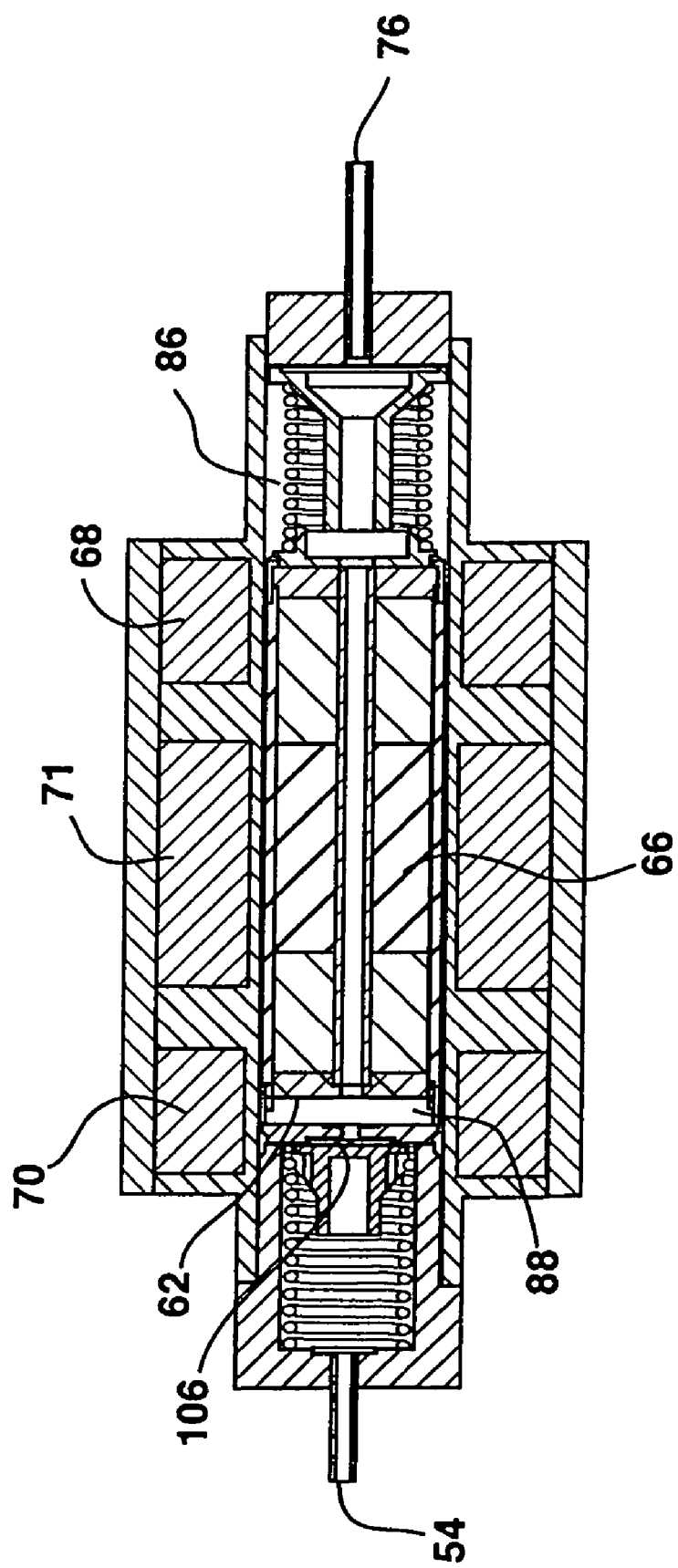
FIG. 11 shows a cross section view of a pump piston for a permanent magnet solenoid pump three-coil embodiment.
Figure 12:
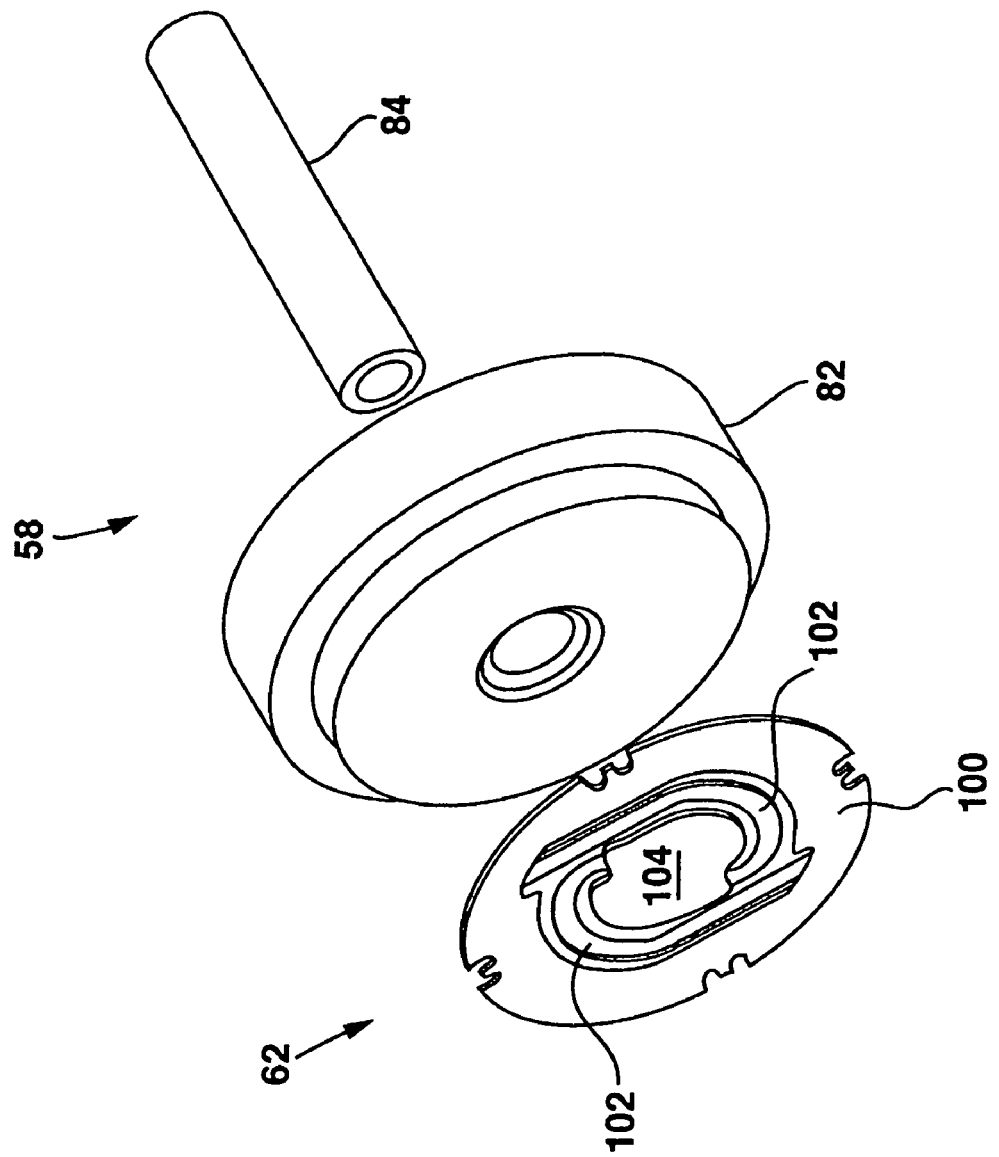
FIG. 12 shows an isometric view of a pump piston end and low profile inlet valve first embodiment.
Figure 13A:
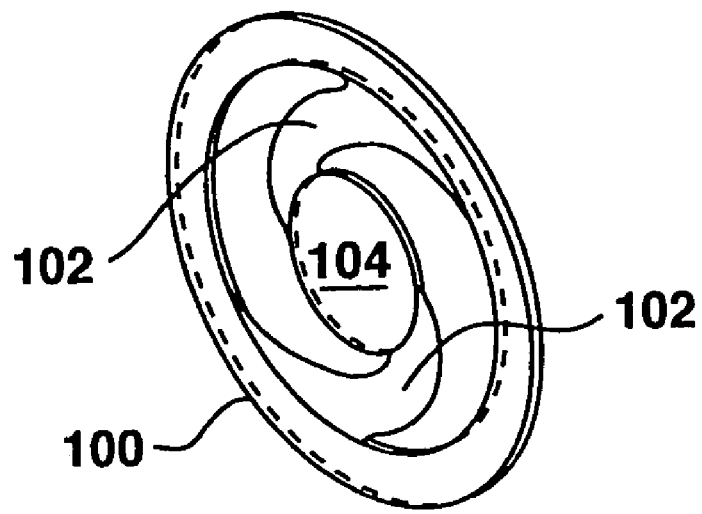
FIGS. 13a-13b show a low profile inlet valve second embodiment.
Figure 13B:
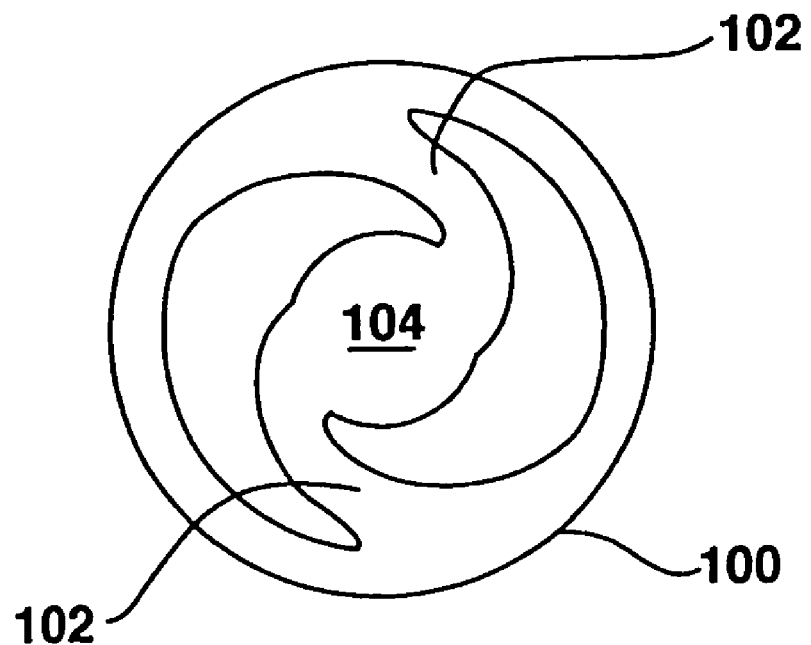
Figure 14A:
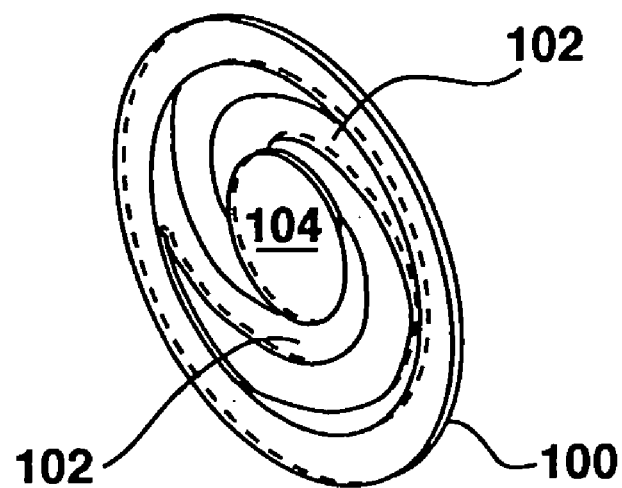
FIGS. 14a-14b show a low profile inlet valve third embodiment.
Figure 14B:
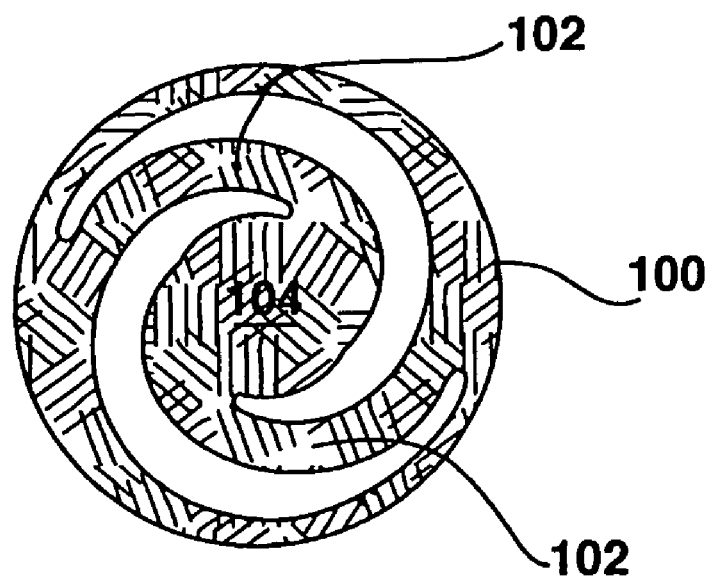

FIGS. 3-6 show views of therapeutic substance delivery device 30 embodiments. An implantable therapeutic substance delivery device 30 with a permanent magnet solenoid pump comprises a housing 41, a therapeutic substance reservoir 42, a power source 44, electronics 46, and a permanent magnet solenoid pump 48. Typically, the therapeutic substance delivery device 30 components are carried in a single housing 41, such as shown in FIGS. 3 and 4, that is manufactured from a material that is biocompatible and hermetically sealed such as titanium, tantalum, stainless steel, plastic, ceramic, and the like. Therapeutic substance delivery device 30 components can also be placed in more than one housing 41, such as shown in FIGS. 5 and 6, that are appropriately coupled. The therapeutic substance reservoir 42 can be placed inside the housing 41 or can be separated from the housing 41 with a fluid coupling such as a tube between the reservoir 41 and the housing 41. The therapeutic substance reservoir 42 is configured to contain a therapeutic substance 36 and may use geometries such as a metal bellows, polyomeric bag, and the like. The therapeutic substance reservoir 42 has a reservoir outlet 52 and can have a septum 40 for refilling the reservoir 42.

The power source 44 is carried in the housing 41. The power source 44 is selected to operate the solenoid pump 48 and electronics 46 such as a lithium ion (Li+) battery, capacitor, and the like. The electronics 46 are coupled to the power source 44 and typically include memory and a controller. The controller can be an Application Specific Integrated Circuit (ASIC) state machine, a gate array, or may include a microprocessor. The electronics 46 are configured to control the solenoid pump 48 infusion rate and can be configured to operate many other features such as patient alarms and the like. The electronics 46 can also include telemetry circuitry configured to receive and send information when the therapeutic substance delivery device 30 is implanted to allow programming of the infusion rate. The solenoid pump 48 is coupled to the electronics 46 and coupled to the therapeutic substance reservoir outlet 52 and configured for pumping therapeutic substance 36 from the therapeutic substance reservoir 42 through an infusion outlet 54 at a programmed rate.

FIGS. 7-11 show a three coil embodiment of the solenoid pump. The permanent magnet solenoid pump 48 comprises a pump cylinder 56, a pump piston 58, a biasing element 60, an inlet valve 62, an outlet valve 64, a permanent magnet 66, a first coil 68, and a second coil 70. The solenoid pump 48 is coupled to the electronics 46, the therapeutic substance reservoir outlet 52, and the infusion outlet 54. The solenoid pump 48 is configured for pumping therapeutic substance 36 from the reservoir 42 through an infusion outlet 54 at a programmed rate.

The pump cylinder 56 has an inlet enclosure 72, an outlet enclosure 74, a therapeutic substance inlet 76, and an infusion outlet 54. The inlet enclosure 72 transitions the pump cylinder 56 to the therapeutic substance inlet 76. The outlet enclosure 74 transitions the pump cylinder 56 to the infusion outlet 54. The therapeutic substance inlet 76 is coupled to a therapeutic substance reservoir outlet 52 and coupled to the inlet enclosure 72 on the pump cylinder 56. Some embodiments can include a piston seal 78 positioned between the pump cylinder 56 and the pump piston 58 to reduce therapeutic substance 36 flow between the pump piston 58 and the pump cylinder 56 and provide other functions. The piston seal 78 can be configured to serve as a guide for the biasing element 60 and to cushion the pump piston 58 at the end of pump piston 58 retraction for the intake stroke. The piston seal 78 is manufactured from a resilient material with good sealing qualities such as synthetic rubber, PTFE, silicone, and the like.

The pump piston 58 is moveable within the pump cylinder 56 and has a piston inlet end 80, a piston outlet end 82, and a piston fluid path 84. The pump piston 58 forms an inlet chamber 86 between the pump piston 58 and the inlet enclosure 72 and a pumping chamber 88 between the pump piston 58 and the outlet enclosure 74. The inlet chamber 86 contains the therapeutic substance 36 that is displaced when the pump piston 58 retracts. The pumping chamber 88 contains the therapeutic substance 36 that is displaced when the pump piston 58 is actuated. The piston fluid path 84 is configured to provide fluid communication between the inlet chamber 86 and the pumping chamber 88 that is controlled by the inlet valve 62. The piston fluid path 84 can take a wide variety of forms such as a central fluid path, a side fluid path, a partial central and partial side fluid path, and the like.

The biasing element 60 is positioned in the pump cylinder inlet chamber 86 between the pump piston 58 and the inlet enclosure 72. The biasing element 60 exerts force on the pump piston 58 to expulse therapeutic substance 36 through the infusion outlet 54. In some embodiments, the biasing element 60 exerts substantially the sole force on the pump piston 58 to expulse therapeutic substance 36 through the infusion outlet 54. The biasing element 60 also provides force to maintain the pump piston 58 in an actuated position until retracted to seal the inlet valve 62 against the outlet enclosure 74 to provide redundant protection against unintended flow of therapeutic substance 36 to the patient 38. The biasing element 60 can be one or more of a wide variety of biasing structures that are selected to provide the desired biasing force on the pump piston 58. The desired force of the biasing element 60 in a particular embodiment is the force required to overcome any frictional losses during the pump piston 58 expulsion stroke, to generate pressure to open the outlet valve 64, and to overcome pressure losses between the infusion outlet 54 and the infusion site 34 that can be located at the distal end of the catheter 32. Some specific embodiments of the biasing element 60 include a spring, a coil spring, and the like.

The inlet valve 62 is carried on the pump piston outlet end 82. The inlet valve 62 can be a variety of inlet valves 62 such as a flapper valve, annular flapper valve, ball valve, reed valve, duckbill valve, poppet valve, and the like. The inlet valve 62 is discussed in more detail later in the detailed description, particularly under FIGS. 12-17. The outlet valve 64 is carried in the outlet enclosure 74 and coupled to the infusion outlet 54. The outlet valve 64 improves solenoid pump 48 safety by substantially preventing unintended flow of therapeutic substance 36 when the reservoir 42 pressure is greater than the infusion site 34 pressure. The outlet valve 64 improves solenoid pump 48 accuracy by maintaining sufficient back pressure to keep the inlet valve 62 closed during therapeutic substance 36 expulsion through the infusion outlet 54 so that addition therapeutic substance 36 is not infused when the reservoir 42 pressure is greater than the infusion site 34 pressure. The outlet valve 64 can be a variety of outlet valves 64 such as a flapper valve, ball valve, reed valve, duckbill valve, poppet valve, and the like.

Some embodiments of the solenoid pump 48 can include an anti-cavitation valve 90 position in fluid communication with the therapeutic substance inlet 76. The anti-cavitation valve 90 substantially prevents therapeutic substance 36 in the inlet chamber 86 from flowing back through the therapeutic substance inlet 76 during pump piston 58 retraction. Since the therapeutic substance 36 cannot flow backwards, pressure in the inlet chamber 86 increases as the pump piston 58 retracts causing the therapeutic substance 36 to flow through the piston fluid path 84 without causing the pump chamber 88 pressure to drop low enough to cause dissolved gasses to come out of solution. Also by substantially preventing the back flow of therapeutic substance 36 through the therapeutic substance inlet 76 during pump piston 58 retraction, piston pump 58 efficiency is improved because wasted therapeutic substance 36 flow is minimized. The anti-cavitation valve 90 can be a wide variety of anti-cavitation valves 90 such as a flapper valve, annual flapper valve, ball valve, reed valve, duckbill valve, poppet valve, and the like. In addition to displacing therapeutic substance 36 that operates the inlet valve 62, outlet valve 64, and anti-cavitation valve 90, the pump piston 58 carries a permanent magnet 66.

The permanent magnet 66 is at least a first permanent magnet 66 having a first pole 92 and a second pole 94. The permanent magnet 66 is carried by the pump piston 58 and acted on by the magnetic fields created by the coils 67 that include at least the first coil 68 and at least the second coil 70. When the first coil 68 and second coil 70 are energized, the coils 67 produce an electromagnetic axial force that acts on the permanent magnet 66 to impart motion to the pump piston 58. In some embodiments, there can be more than one permanent magnet 66 such as a first permanent magnet 66, a second permanent magnet 96, a third permanent magnet 98 and so forth. Also in some embodiments, there can be more than a first coil 68 and second coil 70 such as a third coil 71 and so fourth. When using more than one permanent magnet 66, like poles are positioned adjacent to one another, and there are N−1 operational permanent magnets 66 where N is the number of coils 67 in the range from about 3 to 10. The permanent magnet 66 is manufactured from a hard ferromagnetic material such as samarium cobalt, neodymium, ceramic, alnico, and the like. Since the permanent magnet 66 material is typically not therapeutic substance compatible or biocompatible, the permanent magnet 66 is typically isolated from the therapeutic substance 36 by the piston fluid path 84 and the pump piston 58 sealed is by the piston inlet end 80 and piston outlet end 82. Positioned in operating relationship to the permanent magnet 66 are the first coil 68 and the second coil 70.

When the pump piston 58 is fully positioned toward the inlet enclosure 72, the maximum pump chamber 88 volume is created. The pump chamber 88 has a pump chamber 88 volume comprising a stroke volume and a dead volume. The stroke volume is in the range from about 0.5 micro liters to about 5.0 micro liters. The sum of an inlet valve 62 opening pressure and the outlet valve 64 opening pressure exceeds the maximum pressure of the reservoir 42 less the infusion site 34 pressure to substantially prevent free flow of therapeutic substance 36 to the patient 38. The dead volume is less than half the stroke volume in the range from about 0.25 micro liters to about 2.5 micro liters. The solenoid pump's 48 small dead volume compared to the stroke volume improves the solenoid pump's 48 capability to pass air because of the low vacuum pressure that is typically generated in the pump chamber 88. The inlet valve 62 and outlet valve 64 opening pressures are selected to prevent unintended infusion under extreme operating conditions. Unintended infusion is substantially prevented by selecting the inlet valve 62 opening pressure and the outlet valve 64 opening pressure so the sum of these pressures is greater than the maximum pressure difference between the reservoir 42 and the infusion site 34. For example, unintended infusion is prevented when the reservoir 42 pressure is high and the ambient pressure (typically the same as the infusion site 34 pressure) is low that can occur when the reservoir 42 is full and the patient 38 is exposed to high temperature at high altitude.

The solenoid pump's 48 ability to pass air and operate accurately is a function of the solenoid pump's 48 compression ratio, the reservoir outlet 52 pressure, the infusion outlet 54 pressure, and outlet valve 64 cracking (opening) pressure. For adiabatic systems with ideal gases, the compression ratio in the pump chamber 88 can be expressed as $$CR_{pc} = \frac{V_{pc\,final}}{V_{pc\,initial}} \quad \text{(Equation 1)}$$

where $CR_{pc}$ is the compression ratio in the pump chamber 88, $V_{pc\,final}$ is the final volume in the pump chamber 88 calculated by (stroke volume+pump chamber dead volume) where stroke volume=piston area×piston stroke, and $V_{pc\,initial}$ is the initial volume in the pump chamber 88 also known as the pump chamber dead volume which is also the pump chamber volume remaining after the pump piston 58 has expulsed the stroke volume. The compression ratio in the inlet chamber 86 can be expressed as $$CR_{ic} = \frac{V_{ic\,final}}{V_{ic\,initial}} \quad \text{(Equation 2)}$$

where $CR_{ic}$ is the compression ratio in the inlet chamber 86 and $V_{ic}$ is the volume in the inlet chamber 86, $V_{ic\,final}$=(stroke volume+inlet chamber dead volume), and $V_{ic\,initial}$=(inlet chamber dead volume). From these relationships, it is apparent that pump chamber 88 pressure will be decreasing and inlet chamber 86 pressure will be increasing as the pump piston 58 retracts. For therapeutic substance 36 to flow into the pump chamber 88 when gas bubbles are present, the pressure in the pump chamber 88 during the pump piston 58 stroke must drop substantially below the inlet chamber 86 pressure. For therapeutic substance 36 to flow out of the pump chamber 88, the expulsion pressure must be greater than the infusion outlet 54 pressure. Therapeutic substance 36 flows through the outlet valve 64 when $P_{pc} \geq P_a + P_{ovc}$, where $P_{pc}$ is the pressure in the pump chamber 88, $P_a$ is the ambient pressure at the infusion outlet 54, and $P_{ovc}$ is outlet valve 64 cracking (opening) pressure. By selecting the appropriate outlet valve 64 cracking pressure the risk of unintentional infusion can be substantially eliminated.

FIGS. 12-15b show some of the many potential inlet valve 62 embodiments. The inlet valve 62 comprises a valve body 100, a valve spring 102, and a valve surface 104. The valve spring 102 and valve surface 104 are substantially coplanar when the valve spring 102 is not under load in an un-flexed position. The inlet valve 62 is configured for placement in fluid communication with the reservoir outlet 52 to control the flow of therapeutic substance 36 into the piston pump 48. In some embodiments, the inlet valve body 100 can be attached to the pump piston 58 with spot welds. The geometries of the inlet valve 62 are configured to create an inlet valve 62 dead volume of less than about 0.5 micro liters. The small dead volume improves the piston pump's 48 ability to pass air. The inlet valve 62 operates without the need for a separate spring to decrease dead volume and for simplicity, ease of manufacturing, and reliability. The inlet valve 62 has a low opening pressure of less than about 6895 pascals for rapid operation. In some embodiments, when the piston pump 48 is in an actuated position the inlet valve 62 can be mechanically held closed by the inlet valve 62 contacting the outlet enclosure 74 to substantially prevent the unintended infusion of therapeutic substance 36. This configuration serves as a means for securing to substantially prevent unintended infusion of therapeutic substance 36. The outlet enclosure 74 can be configured with an elastomeric surface 106 (FIG. 11) for the inlet valve 62 to contact to improve the seal between the inlet valve 62 and the outlet enclosure 74. The inlet valve 62 can be considered as a means for inlet valving configured to control the flow of therapeutic substance 36 from the reservoir outlet 52 into a pumping chamber 88. Wide varieties of inlet valve 62 configurations are possible such as a flapper valve, a metal foil flapper valve, and the like.

Figure 15A:
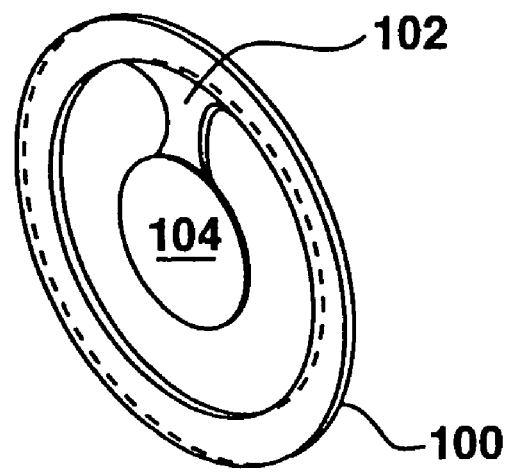
FIGS. 15a-15b show a low profile inlet valve fourth embodiment.
Figure 15B:
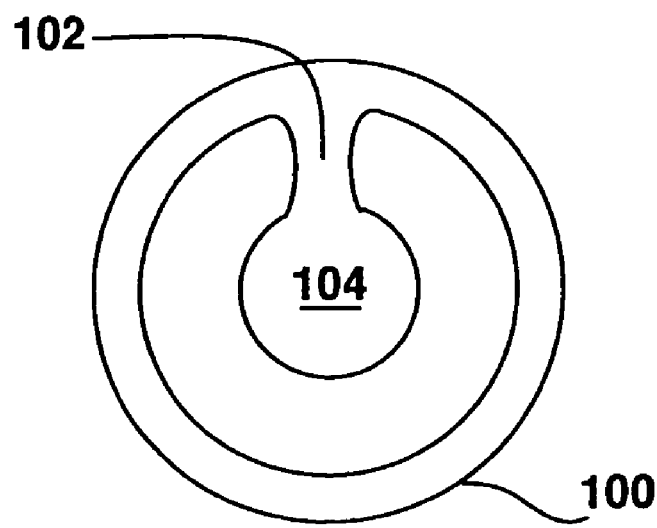

The valve spring 102 can be a single beam spring such as shown in FIGS. 15a-15b, multiple beam springs such as a double beam spring shown in FIGS. 13a-14b, and the like. The valve spring 102 can be configured thinner than the valve surface to increase valve spring 102 flexibility compared to the valve surface 104. The valve spring 102 serves as a means for valve closing. The valve surface 104 can be coated with plastic such as in the range from about 10 to 15 microns thick to improve sealing. The valve surface 104 serves as a means for valving to control flow of therapeutic substance 36 into the pumping chamber 88.

Operation

FIGS. 1-11 show a variety of views that can assist in understanding operation of the implantable therapeutic substance delivery device 30 embodiment. Generally, therapeutic substance delivery device 30 embodiments begin operation by having electronics 46 programmed to operate the permanent solenoid pump 48 to deliver therapeutic substance 36 at a programmed rate. The therapeutic substance 36 is supplied from a therapeutic substance reservoir 42 to a therapeutic substance inlet 76. The solenoid pump 48 generally operates by retracting a pump piston 58 and then actuating the pump piston 58 while operating valves to deliver therapeutic substance 36 through an infusion outlet 54 at a programmed rate. This operation is repeated a predetermined number of times at predetermined intervals to delivery therapeutic substance 36 at the programmed rate. For example, a solenoid pump 48 with a stroke volume of 2.0 micro liters would typically be operated from a maximum of about 10 cycles per second (Hz) to achieve an infusion rate of 1.2 milliliters per minute to a minimum of about 1.0 cycle per hour to achieve an infusion rate of about 48 micro liters per day.

Retracting the pump piston 58 is initiated when a first coil 68 for current flow in a first direction is energized and a second coil 70 for current flow in an opposite direction are energized to create a electromagnetic axial force. The pump piston 58 is retracted when the electromagnetic axial forces acts on a permanent magnet 66 carried on the pump piston 58. While the pump piston 58 is retracting, an inlet valve 62 is opened and a biasing element 60 is loaded. A pump chamber 88 is filled with therapeutic substance 36 through the inlet valve 62 while the pump piston 58 is being retracted. In an embodiment having a piston seal 78, during pump piston 58 retraction the piston seal 78 can also be configured to dampen the shock when the pump piston 58 reaches its fully retracted position. By dampening this shock, the piston seal 78 can reduce some wear and noise that occurs when the pump piston 58 reaches its fully retracted position. In embodiments having an anti-cavitation valve 90, the anti-cavitation valve 90 prevents therapeutic substance 36 in the inlet chamber 86 from flowing back to the therapeutic substance reservoir 42 when the pump piston 58 retracts. The anti-cavitation valve 90 helps maintain higher pump chamber 88 pressures during pump piston 58 retraction, which makes it easier to pass air bubbles.

During pump piston 58 retraction assuming there is anti-cavitation valve 90 and both the inlet chamber 86 and pump chamber 88 are filled with therapeutic substance 36, the pressure in the inlet chamber 86 will increase rapidly due to the incompressibility of liquids which will cause the therapeutic substance 36 to flow through the piston fluid path 84 into the pump chamber 88 without causing the pump chamber 88 pressure to decrease to the level that would cause gasses to come out of solution. After the pump piston 58 is retracted, operation of the solenoid pump 48 continues when the pump piston 58 is actuated.

Actuating the pump piston is initiated when the first coil 68 for current flow in the first direction is de-energized, and the second coil 70 for current flow in the opposite direction is de-energized to collapse the electromagnetic axial force. As the electromagnetic axial force collapses, the biasing element 60 is unloaded, and the pump piston 58 is actuated by the biasing element 60 driving the pump piston 58 toward the outlet enclosure 74. While the pump piston 58 is being actuated, pressure generated in the pumping chamber 88 opens the outlet valve 64. The open outlet valve 64 permits a stroke volume to be expulsed through the infusion outlet 54 while the pump piston 58 is actuated. The therapeutic substance 36 discharged through the infusion outlet 54 is delivered at a programmed rate. In some embodiments during pump piston actuation, the piston seal 78 substantially prevents therapeutic substance 36 from flowing around the pump piston 58 back into the inlet chamber 86. The previously discussed method embodiment elements are presented in a general sequence that is intended to be limiting only when a particular element is required to be sequence in a certain way for the entire method embodiment to be practical. Pump piston actuation can be mathematically characterized.

During piston actuation to expulse therapeutic substance 36, when the pump chamber 88 volume is decreasing and the inlet chamber 86 volume is increasing the following relationships exist. The final pressure in the pump chamber 88 can be express as $$P_{pc\,final} = \frac{P_{pc\,initial}}{CR_{pc}} \qquad \text{(Equation 3)}$$

where $P_{pc\,final}$ is the final pressure in the pump chamber 88, $P_{pc\,initial}$ is the initial pressure in the pump chamber 88, and $CR_{pc}$ is the compression ratio in the pump chamber 88. The final pressure in the inlet chamber 86 can be expressed as $$P_{ic\,final} = \frac{P_{ic\,initial}}{CR_{ic}} \qquad \text{(Equation 4)}$$

where $P_{ic\,final}$ is the final pressure in the inlet chamber 86, $P_{ic\,initial}$ is the initial pressure in the inlet chamber 86, and $CR_{ic}$ is the compression ratio in the pump chamber 88. Therapeutic substance 36 flows through the outlet valve 64 when $P_{pc\,final} \geq P_a + P_{ovc}$ (Equation 5) where $P_{ic}$ is the initial pressure in the inlet chamber 86, $P_a$ is the ambient pressure at the pump outlet, and $P_{ovc}$ is outlet valve 64 cracking (opening) pressure. The above relationships assume that there is an anti-cavitation valve 90, there is no air in the pump chamber 88, and since liquids are essential incompressible $P_{ic}$ decreases as the pump piston 58 is actuated.

Figure 16:
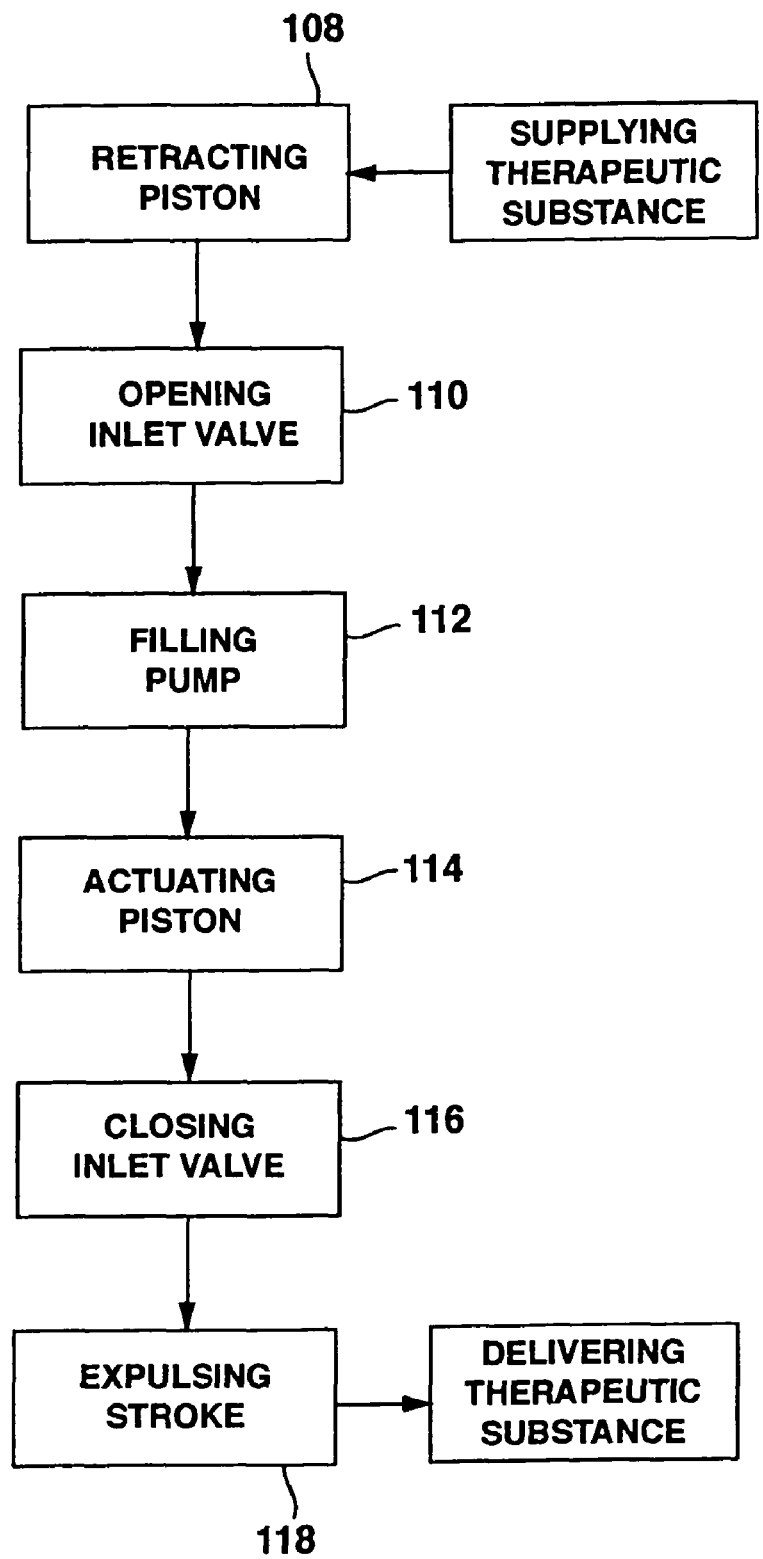
FIG. 16 shows a flow diagram of a method for operating a therapeutic substance delivery device with solenoid pump having a low profile inlet valve embodiment; and, FIG. 17 shows a flow diagram of a method for operating a low profile inlet valve embodiment for a therapeutic substance delivery device.

FIG. 16 shows a flow diagram of a method for operating a low profile inlet valve 62 in a piston pump 48 for an implantable therapeutic substance delivery device 30. The method begins with retracting 108 the pump piston 58 with an electromagnetic axial force acts on the pump piston 58. As the pump piston 58 retracts, the inlet valve 62 opens 110 when a substantially coplanar valve surface 104 moves away from the piston fluid path 84. The pump chamber 88 begins filling 112 with therapeutic substance 36 flowing from a reservoir 42 through the open inlet valve 62. Once the pumping chamber 88 is substantially filled with therapeutic substance 36, the pump piston 58 is actuated 114 by changing the electromagnetic axial force acting on the pump piston 58. The electromagnetic force can be substantially eliminated by de-energizing the coils 67, so a biasing element 60 can actuate 114 the pump piston 58 or the electromagnetic force can be reversed to actuate 114 the pump piston 58. Once the pump piston 58 begins actuation, the inlet valve 62 closes 116 and the inlet valve 62 returns to a substantially coplanar valve surface 104 mating with the piston fluid path 84. With the inlet valve 62 closed 116 and the pump piston 18 actuating 114, a stroke volume is expulsed 118 through an infusion outlet 54. The operation of the inlet valve 62 facilitates passing air contained in the pumping chamber 88 through the infusion outlet 54. In some embodiments, the inlet valve 62 may be held in a closed position when the pump piston 58 is fully actuated to substantially prevent unintended infusion of therapeutic substance 36.

Figure 17:
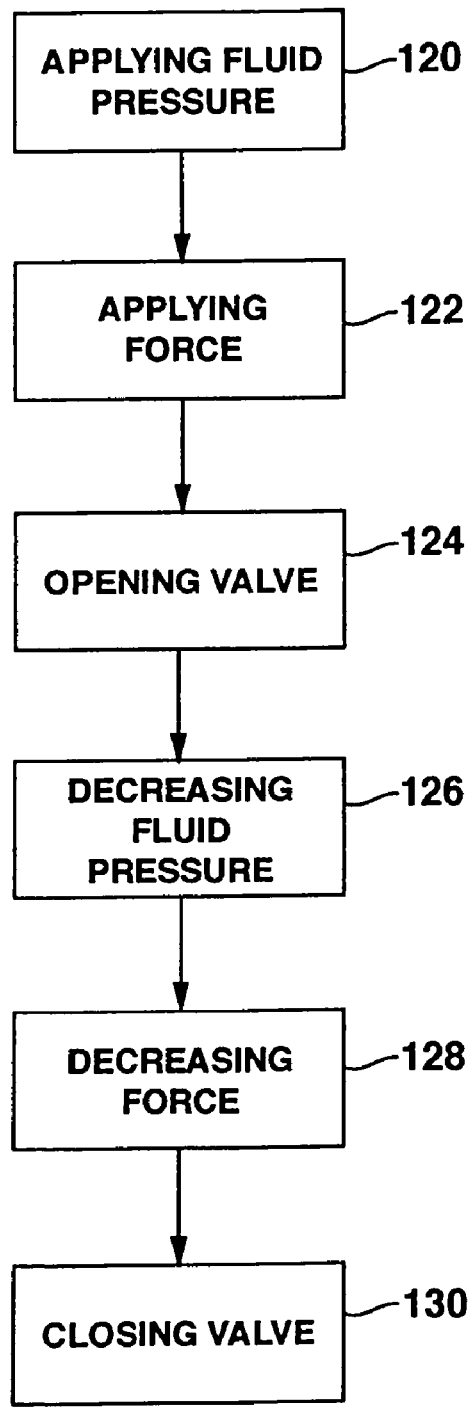

FIG. 17 shows a flow diagram for a method of operating a low profile inlet valve 62 in a piston pump 48 for an implantable therapeutic substance delivery device 30. The method begins when fluid pressure is applied 120 to a valve surface 104 that is greater than the inlet valve 62 release pressure. The fluid-pressure applies a force 122 to a valve spring 102 that is coplanar to the valve surface 104 to flex the valve spring 102. The inlet valve 62 is opened 124 by displacing the valve surface 104 away from a valve seat as the valve spring 102 flexes. As the fluid pressure to the valve surface 104 is decreased 126, the force applied to the valve surface also decreased 128. When the force decreases 128 below the inlet valve 62 release pressure, the inlet valve 62 closes 130 by returning the valve surface 104 back to the valve seat as the valve spring 102 returns to its resting position coplanar to the valve surface 104. In some embodiments, the inlet valve 62 can be held in a closed position when the pump piston 58 is fully actuated to substantially prevent unintended infusion of therapeutic substance 36.

Thus, embodiments of the low profile inlet valve 62 for a piston pump 48 therapeutic substance delivery device 30 are disclosed that reduce dead volume, occupies little residential space, operates rapidly, and have many other improvements. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable therapeutic substance delivery piston pump having a low profile inlet valve, comprising:
 a pump cylinder having an inlet enclosure with a therapeutic substance inlet coupled to a reservoir outlet and an outlet enclosure with an infusion outlet;
 a pump piston moveable within the pump cylinder, the pump piston having a piston fluid path, a piston inlet end and a piston outlet end, the pump piston forming an inlet chamber between the pump piston and the inlet enclosure and a pumping chamber between the pump piston and the outlet enclosure;
 an outlet valve carried on the outlet enclosure, the outlet valve configured to control the flow of therapeutic substance from the pumping chamber into the infusion outlet; and,
 a flat inlet valve carried on the pump piston in operating relation to the piston fluid path, the inlet valve having a valve element and valve spring configured to control the flow of the therapeutic substance from the piston outlet end into the inlet chamber, wherein the valve element comprises a valve surface facing the piston and wherein the valve surface closes the piston outlet end.

2. The implantable therapeutic substance delivery piston pump as in claim 1 wherein the inlet valve is mechanically held closed while the piston pump is fully actuated to substantially prevent unintended infusion of therapeutic substance.

3. The implantable therapeutic substance delivery piston pump as in claim 2 wherein the inlet valve is mechanically held closed by the inlet valve contacting the outlet enclosure.

4. The implantable therapeutic substance delivery piston pump as in claim 3 wherein the inlet valve contacts an elastomeric surface in the outlet enclosure.

5. The implantable therapeutic substance delivery piston pump as in claim 1 wherein the inlet valve creates an inlet valve dead volume of less than about 0.5 micro liters.

6. The implantable therapeutic substance delivery piston pump as in claim 5 wherein the small inlet valve dead volume improves the piston pump's ability to pass air.

7. The implantable therapeutic substance delivery piston pump as in claim 1 wherein the pumping chamber dead volume is less than about 0.5 micro liters.

8. The implantable therapeutic substance delivery piston pump as in claim 1 wherein the inlet valve operates without the need for a separate spring.

9. The implantable therapeutic substance delivery piston pump as in claim 1 wherein the inlet valve has an opening pressure of less than about 6895 pascals.

10. The implantable therapeutic substance delivery piston pump as in claim 1 wherein the valve spring comprises at least one beam.

11. The implantable therapeutic substance delivery piston pump as in claim 1 wherein the valve spring is configured to be thinner that the valve surface to increase the flexibility of the valve spring compared to the valve surface.

12. The implantable therapeutic substance delivery piston pump as in claim 1 wherein the inlet valve comprises a valve body, and wherein the valve element is attached to the valve body by the valve spring.

13. An implantable therapeutic substance delivery piston pump having a low profile inlet valve, comprising:
 a pump cylinder having an inlet enclosure with a therapeutic substance inlet coupled to a reservoir outlet and an outlet enclosure with an infusion outlet;
 a pump piston moveable within the pump cylinder, the pump piston having a piston fluid path, a piston inlet end and a piston outlet end, the pump piston forming an inlet chamber between the pump piston and the inlet enclosure and a pumping chamber between the pump piston and the outlet enclosure;
 an outlet valve carried on the outlet enclosure, the outlet valve configured to control the flow of therapeutic substance from the pumping chamber into the infusion outlet; and,
 a flat inlet valve carried on the pump piston in operating relation to the piston fluid path, the inlet valve comprising a valve body, a valve spring and a valve element, wherein the valve element is attached to the valve body by the valve spring, and wherein the valve element comprises a valve surface that closes the piston outlet to control the flow of the therapeutic substance into the inlet chamber from the piston outlet.

14. The implantable therapeutic substance delivery piston pump as in claim 13 wherein the inlet valve is mechanically held closed while the piston pump is fully actuated to substantially prevent unintended infusion of therapeutic substance.

15. The implantable therapeutic substance delivery piston pump as in claim 14 wherein the inlet valve is mechanically held closed by the inlet valve contacting the outlet enclosure.

16. The implantable therapeutic substance delivery piston pump as in claim 15 wherein the valve surface of the inlet valve contacts an elastomeric surface in the outlet enclosure.

17. The implantable therapeutic substance delivery piston pump as in claim 13 wherein the inlet valve creates an inlet valve dead volume of less than about 0.5 micro liters.

18. The implantable therapeutic substance delivery piston pump as in claim 17 wherein the small inlet valve dead volume improves the piston pump's ability to pass air.

19. The implantable therapeutic substance delivery piston pump as in claim 13 wherein the pumping chamber dead volume is less than about 0.5 micro liters.

20. The implantable therapeutic substance delivery piston pump as in claim 13 wherein the inlet valve operates without the need for a separate spring.

21. The implantable therapeutic substance delivery piston pump as in claim 13 wherein the inlet valve has an opening pressure of less than about 6895 pascals.

22. The implantable therapeutic substance delivery piston pump as in claim 13 wherein the valve spring comprises at least one beam.

23. The implantable therapeutic substance delivery piston pump as in claim 13 wherein the valve spring is configured to be thinner than the valve element to increase the flexibility of the valve spring.

24. A therapeutic substance delivery device comprising:

a pump cylinder comprising:

an inlet enclosure defining a therapeutic substance inlet couplable to a reservoir outlet, and an outlet enclosure defining an infusion outlet;

a pump piston moveable within the pump cylinder, wherein the pump piston defines a piston fluid path extending between a piston inlet and a piston outlet, and further wherein the pump piston forms an inlet chamber between the pump piston and the inlet enclosure and a pumping chamber between the pump piston and the outlet enclosure;

an outlet valve carried on the outlet enclosure, wherein the outlet valve is configured to control fluid communication between the pumping chamber and the infusion outlet of the pump cylinder; and a flat inlet valve carried on the pump piston to control fluid communication through the piston outlet of the piston fluid path into inlet chamber, wherein the inlet valve comprises:

a valve element comprising a valve surface configured to close the piston outlet, and a valve spring coupled to the valve element.

25. The therapeutic substance delivery device as in claim 24 wherein the valve spring comprises at least one beam.

26. The therapeutic substance delivery device as in claim 24 wherein the valve spring is configured to be thinner than the valve element to increase the flexibility of the valve spring.

27. The therapeutic substance delivery device as in claim 24 wherein the inlet valve comprises a valve body, and wherein the valve element is attached to the valve body by the valve spring.

* * * * *